(12) United States Patent
Anderson et al.

(10) Patent No.: US 6,900,315 B2
(45) Date of Patent: May 31, 2005

(54) 2-AMINO-9H-PURIN-9-YL COMPOUNDS AND METHODS FOR INHIBITING/TREATING HIV INFECTIONS AND AIDS RELATED SYMPTOMS

(75) Inventors: Karen S. Anderson, Guilford, CT (US); Adrian Staffin Ray, New Haven, CT (US); Chung K. Chu, Athens, GA (US); Yang Zhenjun, Athens, GA (US)

(73) Assignees: Yale University, Athens, CT (US); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/068,635

(22) Filed: Feb. 5, 2002

(65) Prior Publication Data
US 2003/0018015 A1 Jan. 23, 2003

Related U.S. Application Data
(60) Provisional application No. 60/266,751, filed on Feb. 6, 2001.

(51) Int. Cl.[7] .............. C07D 405/04; A61K 31/52; A61P 31/18
(52) U.S. Cl. ............. 544/277; 514/81; 514/99; 514/211.1; 514/211.11; 514/230.5; 514/249; 514/253.01; 514/253.11; 514/263.2
(58) Field of Search ................ 544/276, 277; 514/81, 99, 211.1, 211.11, 230.5, 253.01, 253.09, 263.22, 249, 263.2

(56) References Cited

U.S. PATENT DOCUMENTS 6,348,587 B1   2/2002   Schinazi et al. ........... 536/25.3

OTHER PUBLICATIONS

Biscone MJ, Pierson TC, Doms RW., Curr Opin Pharmacol. Oct. 2002;2(5):529–33, Medline abstract PMID: 12324254.*

Weber J, Nunn A, O'Connor T, Jeffries D, Kitchen V, McCormack S, Stott J, Almond N, Stone A, Darbyshire J., AIDS. Aug 17, 2001;15(12):1563–8.*

(Continued)

*Primary Examiner*—Thomas C. McKenzie
(74) *Attorney, Agent, or Firm*—Henry D. Coleman; R. Neil Sudol; William J. Sapone

(57) ABSTRACT

The present invention relates to novel compounds, compositions and methods for inhibiting the growth, elaboration and/or replication of HIV in human patients and to the prevention and treatment of human acquired immunodeficiency syndrome (AIDS) and other diseases caused by retroviral infection. More particularly, in preferred aspects, the present invention provides a method for the use of novel prodrug forms of 9-(2,3-Dideoxy-β-D-glycero-pent-2-enofuranosyl) guanine (d4G) for the prevention and treatment of both wild type and drug-resistant Human Immunodeficiency Virus (HIV), the causative pathogen of AIDS. Compounds according to the present invention are based upon the chemical formula:

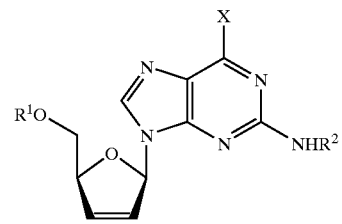

where X is $OCH_3$, $N_3$, $NHCH_3$, $N(CH_3)_2$ or an aminocyclopropyl group;

$R^1$ is H or a $C_1$ to $C_{20}$ acyl or ether group, a phosphate, diphosphate, triphosphate or phosphodiester group; and $R^2$ is H or a $C_1$ to $C_{20}$ acyl or alkyl group.

20 Claims, 4 Drawing Sheets

OTHER PUBLICATIONS

Hawley, Gessner, "The Condensed Chemical Dictonary", 1977, Van Nostrand, New York, p. 349.*
Robins et al Journal of Organic Chemistry, 63(21), 7375–7381 (English) 1998.*
McDowell et al, Antimicrobial Agents and Chemotherapy, 43(12), 2855–2861 (1999).*
De Clercq, E., Clinical Microbiology Reviews 1997, 674–693.
De Clercq, E., J. Medicinal Chem. 38 (14), 1997, 2491–2517.
Mitsuya, H. et al., FASEB J. 5, 1991, 2369–2381.
Parker, W.B. et al., J. NIH Research, 6, 1994, 57–61.
Martin, J.L. et al., Antimicrobial Agents and Chemotherapy 1994, 2743–2749.
Larder, B. A., J. General Virology 75, 1994, 951–957.
Daluge, S. M. et al., Antimicrobial Agents and Chemotherapy 1997, 1082–1093.
Faletto, M. B. et al., Antimicrobial Agents and Chemotherapy 1997, 1099–1107.
Parker, W.B. et al., Antimicrobial Agents and Chemotherapy 1993, 1004–1009.
Vince, R. et al., Biochem. Biophys. Res. Commun. 156, 1988, 1046–1053.
Vince, R. et al., J. Medicinal Chem. 33, 1990, 17–21.
Foster, R. H. et al., Drugs 55(5), 1998, 729–736.
Tisdale, M. et al., Antimicrobial Agents and Chemotherapy 1997, 1094–1098.
White, E.L. et al., Biochem. Biophys. Res. Commun. 161(2), 1989, 393–398.
Parker, W.B. et al., J. Biol. Chem. 266 (3), 1991, 1754–1762.
Harrigan, P. R. et al., J. Infectious Diseases 181, 2000, 912–920.
Miller, V. et al., AIDS 2000, 14 (2), 163–171.
Schinazi, R. F. et al., Antimicrobial Agents and Chemotherapy, 37 (4),1993, 875–881.
Feng, J.Y. et al., Biochemistry 38 (29), 1999, 9440–9448.
Schuurman, R. et al., J. Infectious Diseases 171, 1995, 1411–1419.
Orr, D.C. et al., J. Biol. Chem. 267(6), 1992, 4177–4182.
Kati, W. M. et al., J. Biol. Chem. 267(36), 1992, 25988–25997.
Chu, C. K. et al., Biochemical Pharmacology 37 (19), 1988, 3543–3548.
Perelson, A. S. et al., Science 271, 1996, 1582–1586.
Gao, W.-Y. et al., J. Biol. Chem. 269 (17), 1994, 12633–12638.
Tisdale, M. et al., Proc. Natl. Acad. Sci. USA 90, 1993, 5653–5656.
Bridges, E. G. et al., Biochemical Pharmacology 51, 1996, 731–736.
Dutschman, G. E. et al., Antimicrobial Agents and Chemotherapy 1998, 1799–1804.
Gulick, R. M. et al., J. Infectious Diseases 182, 2000, 1375–1384.
Lambert, D. M. et al., Antiviral Research, 21; 1993, 327–342.
Maga, G. et al., Antimicrobial Agents and Chemotherapy 45 (4), 2001, 1192–1200.
Mulato, A.S. et al., Antiviral Research 36, 1997, 91–97.
Skalski, V. et al., Biochemical Pharmacology, 50 (6), 1995, 815–821.
Snyder, S. et al., Antimicrobial Agents and Chemotherapy 44 (4), 2000, 1051–1058.
Spence, R. A. et al., Science 267, 1995, 988–993.
White, E. L. et al., Antiviral Research, 22, 1993, 295–308.
Wolbach, J. and Capoccia, K. (1999) Nurse Pract. 24, 81–82, 87–90, 92.
Mellors, J. W. et al. (1998) in Fifth Conference on Retroviruses and Opportunistic Infections, Chicago, IL.
Ray, A. S. et al., Antimicrob. Agents Chemother. (2002) 46, 887–891.
U.S. Appl. No. 09/257,130, filed Feb. 25, 1999, Schinazi et al.
J. Heterocyclic Chem., vol. 38, pp. 1297–1306, Nov.–Dec. 2001, Morris J. Robbins, et al.
J. Org. Chem., vol. 62, pp. 1580–1581, 1997, Nobuya Katagiri et al.

* cited by examiner

Synthesis of D4G Prodrug i. Ac₂O/Pyridine/DMF 75° 4h; ii. POCl₃/C₆H₅NEt₂/(n-Bu)₄N⁺Cl⁻/CH₃CN, 100°, 10min; iii. NH₃/CH₃OH, r.t., 6h; iv. (CH₃)₂C(OAc)COBr/CH₃CN, r.t., 3 h; v. Zn/DMF, r.t., 40min; vi. K₂CO₃/CH₃OH/H₂O, r.t., 2h; vii. Cyclopropylamine/ C₂H₅OH, r.t..

Effects of Mycophenolic Acid on Anti-HIV Activity of Nucleosides

*Compounds are more active than what is normally observed because experiments were done using slowly dividing cells. Normally observed $EC_{50}$ vaues in the absence of mycophenolic acid for Carbovir and ddI are 1.2 µM and 20 µM respectively.

Comparision of Synergy Between Abacavir/3TC and cyclo D4G/3TC

Effects of FDA Approved Nucleosides on the anti-HIV Activity of Cyclo D4G

2-AMINO-9H-PURIN-9-YL COMPOUNDS AND METHODS FOR INHIBITING/TREATING HIV INFECTIONS AND AIDS RELATED SYMPTOMS

RELATED APPLICATIONS

This application claims priority from provisional application no. 60/266,751, filed Feb. 6, 2001.

GRANT SUPPORT

This invention was supported by NIH Grant GM49551 and AI25899. The Government retains certain rights in the invention.

FIELD OF THE INVENTION

The present invention relates to novel compounds, compositions and methods for inhibiting the growth, elaboration and/or replication of HIV in human patients and to the prevention and treatment of human acquired immunodeficiency syndrome (AIDS) and other diseases caused by retroviral infection. More particularly, in preferred aspects, the present invention provides a method for the use of novel prodrug forms of 9-(2,3-Dideoxy-β-D-glycero-pent-2-enofuranosyl)guanine (D4G) for the prevention and treatment of both wild type and drug-resistant Human Immunodeficiency Virus (HIV), the causative pathogen of AIDS.

BACKGROUND OF THE INVENTION

HIV-1, the causative agent of acquired immunodeficiency syndrome (AIDS), requires reverse transcriptase (RT) to copy its single stranded RNA genome into a double stranded DNA copy for integration into the host cell genome. Although almost all aspects of HIV-1's life cycle have been targeted (1–3), many of the drugs that have been effective in clinically are nucleoside reverse transcriptase inhibitors (NRTIs). However, treatment with NRTIs is limited by their toxicity to the host (presumably through their interaction with human mitochondrial DNA polymerase γ (4, 5) and the ability of the virus to mutate and acquire resistance (6). Other factors that effect the ability of these inhibitors to reduce viral replication are uptake, transport, metabolism, and incorporation of the drug. All clinically used nucleoside analogs lack 3' hydroxyl groups and are metabolically activated by host cellular kinases to their triphosphate forms. These agents include 3'-azido-3'-deoxythymidine (AZT or Zidovudine), 2',3'-didehydro-2',3'-dideoxythymidine (d4T or Stavudine), β-L-(−)-2',3'-dideoxy-3'-thiacytidine (3TC or Lamivudine), 2',3' dideoxycytodine (ddC or Zalcitabine) and 2',3' dideoxyinosine (ddI or Didanosine).

The structures of the FDA-approved drugs, abacavir (1592U89) and d4T, are unique because they contain a 2',3'-unsaturated bond in the deoxyribose ring. Unlike d4T, abacavir contains a novel carbocyclic ring instead of the sugar ring (FIG. 1). Abacavir has been shown to be a potent and selective inhibitor of HIV-1 replication (7). The metabolic activation of this analog is unique. It is phosphorylated by adenosine phosphotransferase to a monophosphate and further metabolized in several steps to the triphosphate dGTP analog (−) carbovir-TP (CBV-TP)(8, 9). CBV-TP is thought to be the agent responsible for antiviral activity (8, 10–12). Abacavir has a promising pharmacokinetic profile, owing in part to its modified amino group at the 6 position of the purine ring (7, 13). Viral resistance to abacavir develops relatively slowly and cross-resistance between it and other nucleoside analogs is minimal (7, 14, 15). When screened against human DNA polymerases α, β, and γ, CBV-TP was found to be more selective for HIV-1 RT than AZT or dideoxynucleoside triphosphates (16, 17).

Although the resistance profile for abacavir is very good, studies in cell culture and clinical trials have isolated viral mutants in response to prolonged passage or treatment with the drug (14, 18, 19). Three mutations in HIV-1 RT have been found to be necessary to confer as high as an 11-fold resistance: methionine 184 to valine (M184V), leucine 74 to valine (L74V), and lysine 65 to arginine (K65R) or tyrosine 115 to phenylalanine (Y115F). The first mutation isolated in response to abacavir is the M184V mutation ($RT^{M184V}$) and has been associated with a 2 to 4 fold reduction in the virus's susceptibility. HIV-1 with this mutation has shown a 500–1000-fold resistance in the clinic to 3TC (20, 21). Mechanistic studies have shown that $RT^{M184V}$ is 30 to 140 fold more selective than wild type RT ($RT^{WT}$) in distinguishing between dCTP and 3TC-TP depending on the primer template used (22) showing a good correlation between in vitro results and clinical findings.

While a steady-state kinetic analysis of deoxynucleoside triphosphate (dNTP) analogs has given a necessary initial inhibitory evaluation, (16, 17, 23) this approach cannot elucidate the detailed interaction of the drug with RT at the polymerase active site. The reason for the limited scope of this type of analysis is the inability to resolve kinetic steps masked by the rate-limiting step of a reaction. This point is of particular importance with the reaction mechanism of RT. RT follows an ordered reaction pathway (24). The first step involves binding of the DNA or RNA substrate to the enzyme to form an E•DNA complex with a dissociation constant ($K_d$) in the nanomolar range. This step is followed by the binding of a deoxy-nucleoside triphosphate (dNTP) to form the ternary complex (E•DNA•dNTP). The binding of dNTP is a two step process with an initial loose complex followed by a tighter binding complex as the enzyme undergoes a rate limiting conformational change for catalysis ($k_{pol}$) and checks base geometry and pairing. Once the conformational change has taken place and the reactants are properly aligned at the active site for catalysis, the 3' hydroxyl of the elongating strand attacks the α phosphate of the dNTP in a rapid chemical step. The rate-limiting step for the overall reaction ($k_{ss}$) is the release of the elongated DNA from RT. This is the step being analyzed during steady-state kinetic analysis.

The nucleoside compound 9-(2,3-Dideoxy-β-D-glycero-pent-2-enofuranosyl)guanine (d4G) previously has been reported to be inactive against HIV, whereas the carbocyclic analog carbovir has exhibited significant activity. (25, 10) More recent studies suggest that D4G may be unstable under acidic conditions and can retain anti-viral activity if buffered to neural or basic pH. (33)

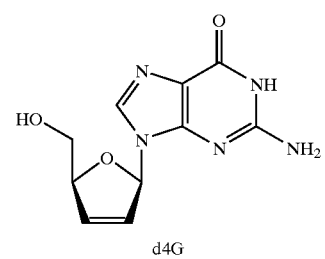

d4G

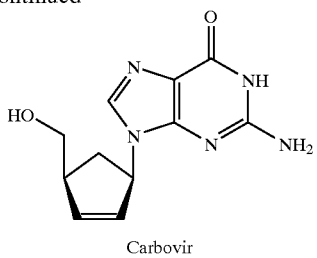

Carbovir

The optimal nucleoside combination therapy should include compounds that i. Interact synergistically (i.e., potentiate anti-HIV activity when combined); ii. Have different resistance profiles; and iii. Are active in all HIV infected cell types. The abacavir/3TC/AZT combination used presently falls short of these goals because of abacavir's lack of synergy and overlapping resistance profile with 3TC.

One area where the abacavir/3TC combination's weaknesses are most apparent is in resting cells. Resting cells are known as important reservoirs for HIV infection.[26] In resting infected cells, deoxy-thymidine analogs have been shown to be relatively ineffective.[27] This dampens AZT's effect in resting cells leaving abacavir and 3TC as the most active agents. The additive interaction between abacavir and 3TC would be sub-optimal under these conditions, however. The abacavir/3TC combinations could also serve to increase subpopulations of MI84V virus that both compounds select for.[28-32] The presence of M184V would decrease the activity of 3TC by around 500-fold[30, 32] leaving abacavir to fight the HIV infection alone with a 2–4 fold decrease in its activity due to the M184V mutation.[31] This may explain the relative ineffectiveness of the drug combination in certain circumstances.

OBJECTS OF THE INVENTION

It is an object of the invention to provide novel compounds which can be used to inhibit the growth, elaboration and/or replication of HIV in human patients or to otherwise treat HIV infections or to reduce the symptomology of AIDS in humans.

It is another object of the invention to provide pharmaceutical compositions for use in treating HIV infections.

It is yet another object of the invention to provide methods which can be used to inhibit the growth, elaboration and/or replication of HIV in human patients or to otherwise treat HIV infections or to reduce the symptomology of AIDS in human patients.

It is still an additional object of the present invention to provide effective drug combination therapy in the treatment of HIV infections and/or AIDS in patients, in certain preferred aspects in instances where traditional compounds and/or combinations of compounds have been shown to be less than optimal and where drug resistant HIV populations are present.

One or more of these and/or other objects of the present invention may be readily gleaned from a description of the invention which follows.

SUMMARY OF THE INVENTION

Figure 1:
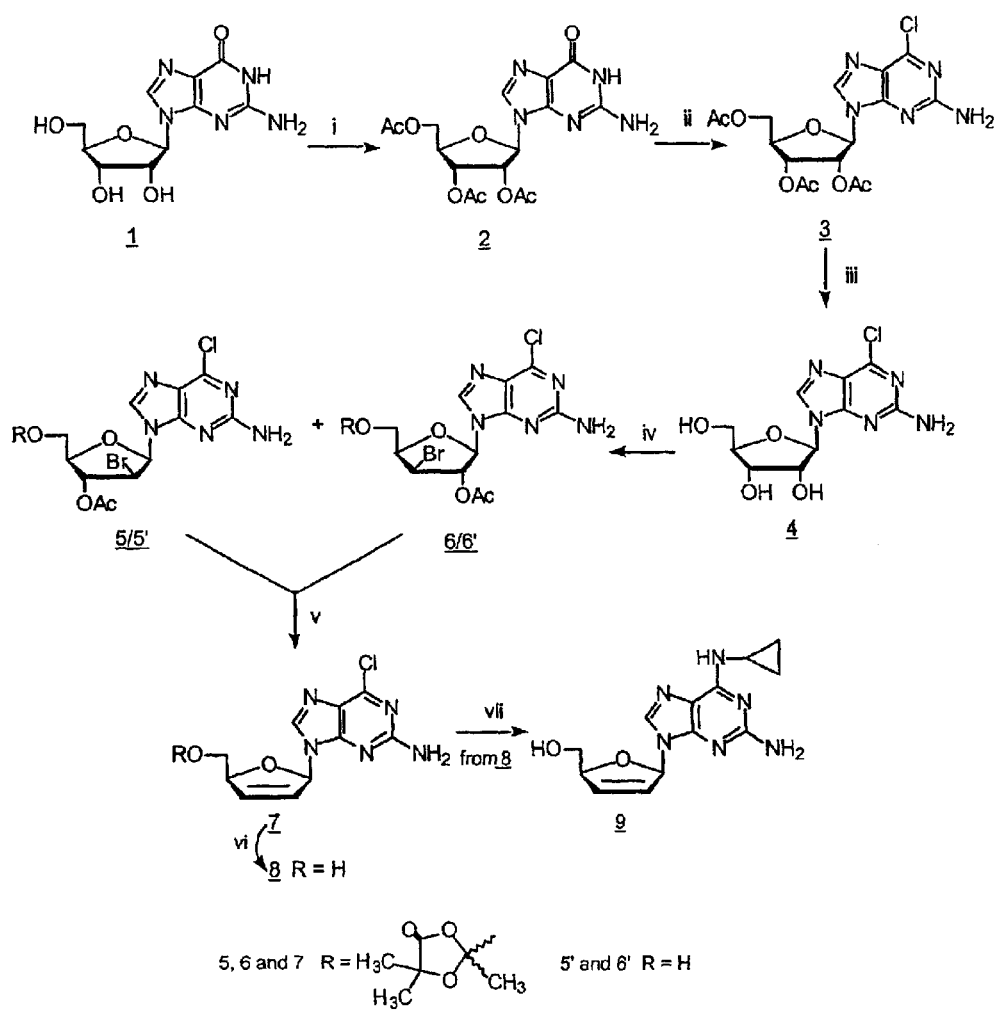
FIG. 1 is a diagrammatic representation of a chemical synthetic scheme which produces cyclo D4G of the present invention.

The present invention also relates to pharmaceutical compositions comprising an effective amount of a compound according to the structure:

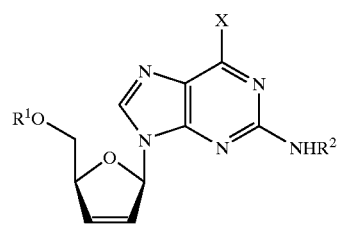

Where X is $OCH_3$, $N_3$, $NHCH_3$, $N(CF_3)_2$ or an aminocyclopropyl group;
$R^1$ is H or a $C_1$ to $C_{20}$ acyl or ether group, a phosphate, diphasphate, triphosphate or phosphodiester group; and
$R^2$ is H or a $C_1$ to $C_{20}$ acyl or alkyl group.

The present invention also relates to pharmaceutical compositions comprising an effective amount of a compound according to the structure:

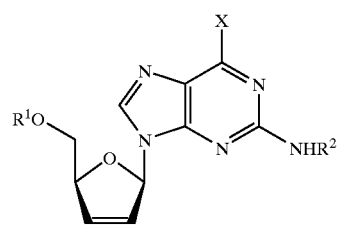

Where X is $OCH_3$, $N_3$, $NHCH_3$, $N(CH_3)_2$ or an aminocyclopropyl group;
$R^2$ is H or a $C_1$ to $C_{20}$ acyl or alkyl group, a phosphate, diphasphate, triphosphate or phosphodiester group; and
$R^2$ is H or a $C_1$ (acetyl) to $C_{20}$ acyl or alkyl group or a pharmaccutically acceptable salt thereof, optionally in combination with a pharmaceutically acceptable carrier, additive or excipient.

In another aspect of the present invention, the present invention relates to a method of inhibiting the growth, elaboration and/or the replication of HIV or otherwise treating an HIV infection in a patient comprising administering to said patient an anti-HIV effective amount of a compound according to the structure:

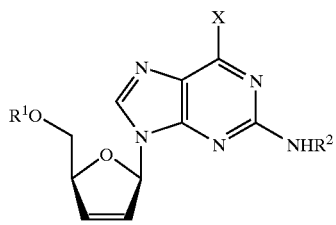

Where X is $OCH_3$, $N_3$, $NHCH_3$, $N(CH_3)_2$ or an aminocyclopropyl group;
$R^1$ is H or a $C_1$ to $C_{20}$ acyl or alkyl group, a phosphate, diphosphate, triphosphate or phosphodiester group; and
$R^2$ is H or a $C_1$ to $C_{20}$ acyl or alkyl group; or a pharmaceutically acceptable salt thereof, optionally in combination with a pharmaceutically acceptable carrier, additive or excipient.

Methods of reducing the likelihood that an individual will contract HIV or that an HIV infection will mature into AIDS comprising administering an effective amount of at least one compound as described above to a person at risk for contracting an HIV infection or an HIV positive patient at risk for AIDS are two prophylactic aspects of the present invention. Methods of treating HIV infections which are drug resistant, and in particular, are AZT and/or 3TC drug resistant, are additional aspects of the present invention.

The present invention also relates to compositions and methods of treating HIV infections and/or AIDS symptoms in patients using combination therapy, said composition comprising an effective amount of one of the dideoxydidehydro guanosine analogs as set forth above in combination with an effective amount of a compound selected from a nucleoside reverse transcriptase inhibitor ("NRTI"), a non-nucleoside reverse transcriptase inhibitor ("NNRTI"), a protease inhibitor ("PI"), other compounds selected from the group consisting of HIV zinc finger inhibitors, such as 1,1'-azobisformamide, cell cycle inhibitors such as hydroxyurea, cytotoxic agents such as LiGLA (lithium gamma linolenic acid) or other agent which inhibit steps in the viral life cycle, or a mixture of these compounds, including compounds which target or inhibit the action of the virally encoded integrase, nucleocapsid protein, gp 120 and gp 41 (such as viral entry inhibitors-i.e., agents which inhibit or reduce the likelihood that HIV will enter CD4 or other cells within the human host). It has unexpectedly been discovered that combined therapy of one of the dideoxydidehydroguanosine analogs of the present invention with at least one compound selected from the group consisting of a NRTI, a NNRTI, a protease inhibitor, a HIV zinc finger inhibitor, a cell cycle inhibitor, a general anti-HIV cytoxic agent or other anti-HIV agent which functions to inhibit HIV life cycle steps, as/otherwise described herein, is a particularly effective treatment for HIV infections and/or AIDS in patients.

Combined compositions and/or methods of treatment which utilize a combination of agents as described above are particularly effective against drug resistant strains of HIV, in particular, those strains which have exhibited resistance to anti-HIV agents, and in particular, AZT and/or 3TC. In many instances, the combination therapy results in an unexpected synergistic activity in the treatment of HIV infections and/or AIDS. In preferred aspects of the present invention, cyclo D4G (also referred to herein as CD4G, a compound according to the present invention where X is a cyclopropylamine group and $R^1$ and $R^2$ are preferably both H) is combined with either AZT and/or 3TC to produce an effective combination therapy against HIV and in particular, strains of HIV which exhibit resistance against either or both of AZT and 3TC (especially those strains which exhibit or express the M184V mutation). In particularly preferred aspects of the present invention, either 3'-azidothymidine (AZT) or lamivudine (also known as epivir or 3TC), preferably both in effective amounts are administered in combination with one of the guanosine compounds according to the present invention for the treatment of HIV infections and/or AIDS in patients.

Methods of treating HIV infections and/or the symptomology of AIDS in patients is another aspect of the present invention. Treatment of drug-resistant strains of HIV and in particular, AZT or 3TC resistant strains, are another preferred aspect of the present invention. It has unexpectedly been discovered that a combination of an effective amount of a dideoxydidehydroguanosine analog as described herein, preferably where X is an aminocyclopropyl group, with an effective amount of either AZT or 3TC, or preferably, both AZT and 3TC, results in a therapeutic combination which provides synergistic anti-HIV activity in the treatment of HIV infections and/or the symptomology of AIDS. Other combination therapies as described in detail herein represent alternative embodiments of the present invention.

In preferred aspects of the present invention, X is an aminocyclopropyl group and both $R^1$ and $R^2$ are both H (referred to herein primarily as CD4G).

DETAILED DESCRIPTION OF THE INVENTION

The term "patient" is used throughout the specification to describe a human patient, to whom treatment, including prophylactic treatment, with the compositions according to the present invention is provided. For treatment of those infections, conditions or disease states which are specific for a specific human patient, the term patient refers to that specific patient.

The term "acyl" is used throughout the specification to describe a group at the 5' position of the nucleoside analog (i.e., at the free hydroxyl position in the dioxolanyl moiety) which contains a $C_1$ to $C_{20}$ hydrocarbon, including a substituted hydrocarbon, preferably a linear, branched or cyclic alkyl chain. The acyl group at the 5' position, in combination with the 5' hydroxyl group results in an ester, which, after administration, may be cleaved to produce the free nucleoside form of the present invention. Acyl groups according to the present invention may be represented by the structure:

where $R^3$ is a $C_1$ to $C_{20}$ hydrocarbon or substituted hydrocarbon group, such as a linear, branched or cyclic alkyl chain, alkoxyalkyl, aryloxyalkyl, such as phenoxymethyl, aryl, alkoxy, among others. Preferred acyl groups are those where $R^3$ is $C_1$ to $C_3$. Acyl groups according to the present invention also include, for example, those acyl groups derived from benzoic acid and related acids, 3-chlorobenzoic acid, succinic, capric and caproic, lauric, myristic, palmitic, stearic and oleic, among numerous others including mesylate groups. One of ordinary skill in the art will recognize the acyl groups which will have utility in the present invention, either to synthesize the target pharmaceutical compounds or as prodrugs of the nucleosides according to the present invention. The term "ether group" is used to describe substituents at $R^1$ of compounds according to the present invention, such that $R^1$ forms an ether group with the attached sugar synthon. $R^1$ is preferably a $C_1$ to $C_{20}$ hydrocarbon or substituted hydrocarbon and is more preferably an alkyl group (whether linear, branched or cyclic), including a $C_1$ to $C_3$ alkyl group.

The term "phosphate ester" or "phosphodiester" is used throughout the specification to describe mono-phosphate groups at the 5' position of the didehydro sugar synthon which are diesterified such that the phosphate group is rendered neutral, i.e., has a neutral charge. Phosphate esters for use in the present invention include those represented by the structures:

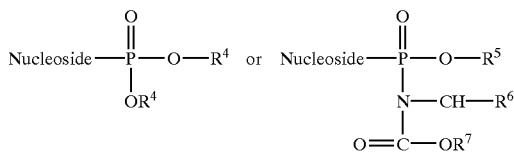

where $R^4$, $R^6$ and $R^7$ are selected from a $C_1$ to $C_{20}$ linear, branched or cyclic alkyl group, alkoxyalkyl, aryloxyalkyl, such as phenoxymethyl, aryl and alkoxy, among others, and $R^5$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R^4$ is a $C_1$ to $C_{20}$ is a linear or branched chain alkyl group, more preferably a $C_1$ to $C_3$ alkyl group.

The term "pharmaceutically acceptable salt" is used throughout the specification to describe any pharmaceutically acceptable salt form of a nucleoside compound according to the present invention which, upon administration to a patient, provides directly or indirectly the nucleoside compound or an active metabolite of the nucleoside compound. In general, the compounds according to the present invention, because of the presence of a guanine base, readily form salts. In addition, the mono-, di- and tri-phosphate forms of the nucleoside compounds according to the present invention will form salts on the phosphate moiety. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art.

The term "effective amount" is used throughout the specification to describe concentrations or amounts of compounds according to the present invention which may be used to produce a favorable effect within the context of the administration of a compound. An effective amount includes that amount which produces a favorable change in the disease or condition treated, whether that change relates to the inhibition of the growth, replication and/or elaboration of the retrovirus (preferably, HIV), including, reducing the likelihood of or preventing a patient contracting an HIV infection or a reduction in severity or elimination of the symptoms associated with a condition or disease state, whether that condition or disease state is an HIV infection or AIDS.

The term "inhibitory effective concentration" or "inhibitory effective amount" is used throughout the specification to describe concentrations or amounts of compounds according to the present invention which substantially or appreciably inhibit the growth or replication of susceptible viruses, especially HIV, itself or in combination with another agent.

The term "therapeutic effective amount" is used throughout the specification to describe concentrations or amounts of compounds according to the present invention which are therapeutically effective in treating retroviral infections, in particular, HIV infections in human, alone or in combination with another agent. In many instances according to the present invention, an inhibitory effective is the same as a therapeutic effective amount.

The term "dideoxy" is used throughout the specification to describe ribofuranosyl moieties which contain hydrogens rather than hydroxyls or other substituents at the 2' and 3' positions of the sugar synthon.

The term "didehydro" is used throughout the specification to describe ribofuranosyl moieties which contain a double bond between the 2' and 3' positions of the sugar synthon. For example, 2',3'-didehydro refers to a ribofuranosyl moiety containing a double bond between the 2' and 3' carbons of the sugar.

The term "aminocyclopropyl" is used throughout the present application to describe a group according to the structure:

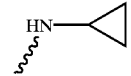

The aminocyclopropyl group may be one of the X substituents' on the guanosine analogs according to the present invention and is the preferred substituent on dideoxydidehydro guanosine compounds according to the present invention.

The term "nucleoside reverse transcriptase inhibitors" or "NRTI" refers to nucleoside compounds which lack a 3' hydroxyl group and serve to chain terminate viral transcripts which are synthesized by the reverse transcriptase of HIV. Examples of such inhibitors include, for example, A7-T (Zidovudine or Retrovir), 3TC (Lamivudine, Epivir), ddC (Zalcitavine, Hivid), FTC, (Emtricitabine, Coviracil), D4FC (DPC 817), D4T (stavudine, Zerit), Abacavir, ddI (Didanosine, Videx), PMPA, (Tenofovir), Bis(POC)PMPA (Tenofovir Disoproxyl Fumate) and dideoxy-didehydro guanosine compounds according to the present invention, among a number of others.

The term "non-nucleoside reverse transcriptase inhibitors" or "NNRTI" refers to compounds which are non-nucleosides and which inhibit HIV reverse transcriptase generally by binding to a location on the reverse transcriptase enzyme and slowing the rate of catalysis. Examples of NNRTIs for use in the present invention, include, for example, Nevirapine (Viramune), Delavirdine (Rescriptor), Efavirenz (Sustiva), Emivirine (Coactinon), TIBO, TIBO-derivatives, GW420 867X (from Glaxo Wellcome) and UC 781 (from Uniroyal Corporation), among numerous others. Other non-nucleoside reverse transcriptase inhibitors include, for example, Foscamet (PFA, Foscavir) and PFA derivatives, which bind and inhibit HIV reverse transcriptase at sites other than the those inhibitors listed above, and compounds disclosed in U.S. Pat. Nos. 6,180,654 and 6,156,759, relevant portions of which are incorporated by reference herein.

The term "protease inhibitor" refers to compounds which block or inhibit the virally (HIV) encoded protease enzyme. Protease inhibitors which can be used in the present invention include, for example, Saquinavir (Invirase, Fortovase), Amprenavir (Agenerase), Indinavir (Crixivan), Nelfinavir (Viracept), Ritonavir (Norvir), Tipranavir (from Boehringer Ingelheim), lopinavir (from Abbott Laboratories), GW433 908 (from Glaxo Wellcome), Lasinavir (from Novartis), as well as numerous others, including compounds which are described in U.S. Pat. Nos. 6,331,542; 6,329,502; 6,313,296; 6,313,110; 6,313,094; 6,291,687; 6,284,777; 6,284,767; 6,281,367; 6,271,235; 6,251,906; 6,232,342; 6,008,228; 5,914,232; 5,827,827; 5,776,933; and 5,683,999, among numerous others, relevant portions of which are incorporated by reference herein.

The term "integrase inhibitor" is used to describe a compound which inhibits virally encoded integrase. Integrase inhibitors for use in the present invention include, for example, benzodiazepine hydrazides, as well as other agents disclosed in U.S. Pat. Nos. 6,335,017; 6,333,323; 6,306,891; 6,271,402; 6,262,055; 6,245,806; 6,124,327; 6,110,716; 5,939,414; 5,866,575; and 5,759,842, among numerous others, relevant portions of which are incorporated by reference herein.

The term "nucleocapsid inhibitor" is used to describe a compound which inhibits the formation of or bind to nucleocapside protein of the virus, including compounds or compositions disclosed in U.S. Pat. No. 6,316,190, relevant portions of which are incorporated by reference herein.

The term "viral entry inhibitor" is used to describe compounds which inhibit glycoprotein 120 (gp 120) and 41 (gp 41) and entry of the virus into a cell, in particular, a CD4 cell, including compounds or compositions disclosed in U.S. Pat. Nos. 6,333,395; 6,258,932; 6,258,599; 6,245,737; 6,068,973 and 6,060,065, relevant portions of which are incorporated by reference herein.

The term "combination therapy" or "co-administration" is used to describe the administration of at least two anti-HIV agents (one of which is a dideoxydidehydro guanosine compound according to the present invention) at the same time (i.e., such that an effective amount or concentration of one agent is found in the patient at the same time as another agent, regardless of the time at which and duration for which the two agents have been administered) for the treatment or prevention of an HIV infection or the symptoms of AIDS. Although in certain preferred embodiments according to the present invention the administration of two anti-HIV agents at approximately the same time is preferred, in general, the invention contemplates coadministration of agents such that overlap of effective amounts or concentrations of active compounds may be found in the patient regardless of when the agents are co-administered.

The term "prophylactic" or "prevention" is used to describe a method in which an agent is used to reduce the likelihood that a patient will succumb to an HIV infection or an HIV infection will mature into AIDS or worse and become AIDS in a patient. Compounds and methods according to the present invention, whether using a single anti-HIV agent or combination therapy according to the present invention, may be used prophylactically to reduce the likelehood that a pateint will succumb to an HIV infection or that an HIV infection will worsen to become AIDS in that patient.

In general, the most preferred anti-viral, especially anti-HIV compounds, according to the present invention include those which are less cytotoxic to the host cells and more active to the targeted virus. Certain of the compounds, in pharmaceutical dosage form, may be used as prophylactic agents. These may be particularly appropriate as antiviral agents, and in particular, anti-HIV agents. Certain of the present compounds are especially preferred as prophylactic agents for the prevention of AIDS given their very low toxicity to humans, and their effectiveness against HIV.

The dideoxydidehydro guanosine compounds according to the present invention are produced by synthetic methods which are readily known to those of ordinary skill in the art and include various chemical synthetic methods as elaborated in significantly more detail in the Examples which follow. In general, compounds according to the present invention are synthesized by acetylating guanosine (Scheme 1, FIG. 1) to form the triacetyl derivative and then chlorinating the 6 position of the guanine base to form the 6-chloro-2-amino derivative which is treated with methanolic ammonia to obtain the free carbohydrate derivative which is reacted with α-acetoxyisobutyryl bromide to obtain a mixture of the 3' (2')-bromoacetate derivative which is subjected to zinc reduction to produce the 2',3'-unsaturated 6-chloro guano sine nucleo side. Reaction of the 6-chlorounsaturated nucleoside analog with weak base such as potassium carbonate ($K_2CO_3$) followed by the appropriate nucleophilic compound (such as sodium methoxide to provide a methoxide group, lithium or sodium azide to provide an azide group, or methyl amine or dimethylamine will afford the nucleoside prodrug compounds of the present invention.

During chemical synthesis of the various compositions according to the present invention, one of ordinary skill in the art will be able to practice the present invention without engaging in undue experimentation. In particular, one of ordinary skill in the art will recognize the various steps that should be performed to introduce a particular substituent at the desired position of the base or a substituent at the desired position on the sugar moiety. In addition, chemical steps which are taken to "protect" functional groups such as hydroxyl or amino groups, among others, as well as "de-protect" these same functional groups, will be recognized as appropriate within the circumstances of the syntheses.

The therapeutic aspect according to the present invention relates to methods for treating retroviral infections in animal or human patients, in particular, HIV infections in humans comprising administering anti-viral (anti-HIV) effective amounts of the dideoxydidehydro guanosine compounds according to the present invention to inhibit the growth, elaboration or replication of the viruses in the animal or human patient being treated. Prophylactic methods for reducing the likelihood that a patient will succumb to an HIV infection and/or AIDS using the dideoxydidehydro guanosine compounds according to the present invention is another aspect of the present invention. Co-administration of at least two anti-HIV agents in the treatment or prevention of an HIV infection or AIDS in a patient are alternative embodiments of the present invention.

Pharmaceutical compositions based upon these novel chemical compounds comprise the above-described compounds in a therapeutically effective amount for treating a viral, preferably a HIV infection, optionally in combination with a pharmaceutically acceptable additive, carrier or excipient. One of ordinary skill in the art will recognize that a therapeutically effective amount will vary with the infection or condition to be treated, its severity, the treatment regimen to be employed, the pharmacokinetics of the agent used, as well as the patient (animal or human) treated. An alternative embodiment of the pharmaceutical aspect of the present invention relates to pharmaceutical compositions comprising an effective amount of at least one dideoxydidehydro guanosine compound according to the present invention in combination with an effective amount of at least one other anti-HIV compound. In certain preferred aspects of the present invention the drug combination may formulated within the same dosage form.

In the pharmaceutical aspect according to the present invention, the compound according to the present invention is formulated preferably in admixture with a pharmaceutically acceptable carrier, excipient or additive. In general, it is preferable to administer the pharmaceutical composition in orally-administrable form, but certain formulations may be administered via a topical, parenteral, intravenous, intramuscular, transdermal, buccal, subcutaneous, suppository or other route. Intravenous and intramuscular formulations are preferably administered in sterile saline. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or other vehicle, for example, may be easily accomplished by minor modifications (salt formulation, esterification, etc.) which are well within the ordinary skill in the art. It is also well within the routineer's skill to modify the route of administration and dosage regimen of a particular compound in order to manage the pharmacokinetics of the present compounds for maximum beneficial effect in patients.

In certain pharmaceutical dosage forms, certain pro-drug form of the compounds, especially including acylated (acetylated or other) derivatives, pyridine esters and various salt forms of the present compounds are preferred. One of ordinary skill in the art will recognize how to readily modify the present compounds to preferred pro-drug forms to facilitate delivery of active compounds to a targeted site within the host organism or patient. The routineer also will take advantage of favorable pharmacokinetic parameters of the pro-drug forms, where applicable, in delivering the present compounds to a targeted site within the host organism or patient to maximize the intended effect of the compound.

The amount of compound included within therapeutically active formulations according to the present invention is an effective amount for treating the infection or condition, in its most preferred embodiment, an HIV infection, or AIDS. In general, a therapeutically effective amount of the present compound in dosage form usually ranges from slightly less than about 0.01 mg/kg to about 25 mg/kg of the patient or considerably more, depending upon the compound or compounds used, the condition or infection treated and the route of administration. In the case of HIV infections, the compound(s) is preferably administered in amounts ranging from about 0.5 mg/kg to about 25–50 mg/kg. In the case of the use of preferred compounds according to the present invention for the treatment of HIV or AIDS, the compound is preferably administered in an amount ranging from about 0.5 mg/kg to about 25 mg/kg, depending upon the pharmacokinetics of the agent in the patient. Coadministration of compounds according to the present invention follow the above-described guidelines. Each compound may be administered in effective amounts within the ranges described above.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration. Coadministration of compounds may be in a single dosage form or may be dosed in more than one form and route of administration. Oral dosage forms are preferred for use in the present invention.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

In particularly preferred embodiments according to the present invention, the compounds and compositions are used to treat HIV infections in humans, including AIDS. Preferably, to treat HIV infections, the compositions will be administered in oral dosage form in amounts ranging from about 50 micrograms up to about 500 mg or more up to four times a day. The present compounds are preferably administered orally, but may be administered parenterally, topically or in suppository form.

The compounds according to the present invention may advantageously be employed prophylactically to prevent infection or to prevent the occurrence of clinical symptoms associated with the viral infection (AIDS). Thus, the present invention also encompasses methods for the therapeutic or prophylactic treatment of viral infections, and in particular HIV infections. This prophylactic method comprises administering to a patient in need of such treatment an amount of a compound or compounds according to the present invention effective for alleviating, and/or preventing the viral infection, in particular, an HIV infection or reducing the likelihood that an HIV infection will deteriorate into AIDS. In the prophylactic treatment according to the present invention, it is preferred that the antiviral compound or compounds utilized should be as low in toxicity and preferably non-toxic to the patient. It is particularly preferred in this aspect of the present invention that the compound or compounds which are used should be maximally effective against the virus and should exhibit a minimum of toxicity to the patient. In the case of the present compounds, one or more of these compounds may be administered within the same dosage range for therapeutic treatment (i.e., about 250 micrograms up to about 500 mg from one to four times per day for an oral dosage form) as a prophylactic agent to prevent the rapid proliferation of HIV or alternatively, to prolong the onset of AIDS in a patient.

In addition, compounds according to the present invention may be administered alone or in combination with other agents, especially including other compounds of the present invention. Certain compounds according to the present invention may be effective for enhancing the biological activity of certain agents according to the present invention by reducing the metabolism or inactivation of other compounds and as such, are co-administered for this intended effect. In the case of the present compounds, these may be effectively combined with any one or more of the standard anti-HIV agents which are presently utilized including AZT, 3TC, ddC, ddI, carbovir, abacavir, among numerous others, well known in the art and as otherwise described hereinabove.

While not being limited by way of theory, it is believed that the compounds according to the present invention primarily induce their inhibitory effect on the growth or replication of HIV by functioning as anti-metabolites of the reverse transcriptase enzyme of the virus.

The present invention is now described, purely by way of illustration, in the following examples. It will be understood by one of ordinary skill in the art that these examples are in no way limiting and that variations of detail can be made without departing from the spirit and scope of the present invention.

EXAMPLES

Chemical Synthesis

Experimental

2',3',5'-Tri-O-acetyl-guanosine (2) by the method of Gerster, et al., *J. Org. Chem.*, 1963, 28, 945.

To a suspension of guanosine (1) (Dried in vacuo over $P_2O_5$ for 2 days at 100°, 10.6 g, 37.6 mmole) in DMF (distilled from $P_2O_5$, 30 ml), $Ac_2O$ (re-distilled, 22.4 ml) and pyridine (distilled from KOH, 11.2 ml) were added. The mixture was heated with stirring at 75°. The mixture became clear solution after 1.5 h. Heating was continued for another 2.5 h. The resulting clear solution is filtered while hot, cooled to temperature, and evaporated in vacuo to afford a heavy, crystalline suspension. A portion (35 ml) of 2-methyl-2-propanol was added. The suspension is filtered, and the filter cake was washed with 2-methyl-2-propanol and dried. This crystalline is the hemi-solvate with $HCONMe_2$, and was added to boiling 2-methyl-2-propanol, and the suspension was boiled under reflux for 5 min, cooled and refrigerated for 10 h at −5°. After filtration, the white crystalline was dried in air overnight, dried in vacuo over $P_2O_5$ for 2 days at 80°, to give white powder (12.0 g, 78.4%, mp:227–230°, lit. 226–231°).

2-Amino-6-chloro-9-(2,3,5-tri-O-acetyl-β-D-ribofuranosyl) purine (3) following the method of Manning, S. J. and Townsend, L. B., *Nucleic Acid Chemistry, Improved and New Synthetic Procedures Methods and Techniques*, Part 2, 589–594, Edited by Townsend, L. B. and Tipson, R. S., A Wiley-Interscience Publication, New York, 1978.

Acetonitrile (60 ml, refluxed over $P_2O_5$ and distilled there from) was added into a dried flask containing dry 2 (12.0 g, 29.3 mmole) and n-tetrabutylammonium chloride (5.70 g, 20.9 mmole). N,N-Diethylaniline (5.70 ml, 29.3 mmole) and phosphoryl cloride ($POCl_3$, 16 ml, 175.2 mmole, freshly distilled, immediately before use) were added to the magnetically stirred solution at room temperature. The flask was placed in oil bath which was preheated to 100°, and the solution was boiled under reflux with stirring for 10 min. Volatile material are immediately flash-evaporated under vacuo. The yellow foam resulting is stirred with crushed ice for 15 min. The layers were separated, the aqueous was washed with chloroform (cold, 3×60 ml), and the organic phase are combined, successively washed with cold water (6×30 ml) and 5% aqueous sodium hydrogencarbonate solution (to pH 7.0), dried (magnesium sulfate) for 1 h, filtered and evaporated. The residue was purified with silic gel chromatography to give 3 (8.0 g, colorless syrup, 64.0%).

2-Amino-6-chloro-β-D-9-β-D-ribofuranosylpurine (4) by the method of Gerster, et al., *Synthetic Procedures in Nucleic Acid Chemistry*, Edited by Zorbach, W. W. and Tipson, R. S., A Wiley-Intersciens, New York, Vol. 1, pp. 242–243.

Compound 3 (8.0 g, 18.8 mmole) was added to anhydrous methanol (dried over 4 Å molecular sieves) pre-saturated with anhydrous ammonia at −10°. The solution is stirred at room temperature for 6 h. Then it was evaporated under diminished pressure at room temperature to afford a slurry. Anhydrous diethyl ether (30 ml) was added, and the solid is collected by filtration, washed with ether, and air dried to give 4 (white powder, 7.0 g, 94.0%, m.p. 163–1166°, lit. 165–167°).

2-Amino-6-chloro-9-5-O-(2,5,5-trimethyldioxolan-4-on-2-yl)-2,3-dideoxy-β-D-glycero-pent-2-eno-furanosyl}purine (7) and 2-Amino-6-chloro-9-(2,3-dideoxy-β-D-glycero-pent-2-enofuranosyl) purine (8) by the method of Robins, et al., *J. Org. Chem.* 1995, 60, 7902 and Mansuri, et al., *J. Org. Chem.* 1989, 54 (20), 2217.

Compound 4 (dried over $P_2O_5$ for 24 at 60°, 1.0 g, 3.31 mmole) was suspended in acetonitrile (dried over, and distilled from, $CaH_2$ before use, 50 ml). α-Acetoxy-isobutyryl bromide (α-AIBBr, 1.80 ml, mmole) was added dropwise slowly at −40° under $Ar_2$. The mixture was stirred at room temperature for 3 h (solution was obtained at 1.5 h). Saturated $NaHCO_3/H_2O$ (60 ml) was added cautiously at −0°, and the solution was extracted (EtOAc, 3×50 ml). The combined organic phase was washed (brine), dried ($Na_2SO_4$), filtered and evaporated to give solid foam which was a mixture of 5/5' and 6/6' (0.85 g) Zn (dust was activated in EtOH (95%)/AcOH (3:1) for 5 min, washing by decantation (EtOH, 3×, DMF, also for reduction, which is dried and distilled over $CaH_2$, and heated and distilled again over ninhydrin in vacuo, 2×). Then it was transferred to the solution of 5/5' and 6/6' in DMF (16 ml). Stirring was continued at room temperature for 40 min. After filtration and evaporation (<30°) in vacuo, the residue was purified with silic gel chromatography eluting with n-hexan/$CHCl_3$/MeOH to give 7 (solid foam, 650 mg, 49.7% from 4) and 8 (solid foam, 25 mg, 2.82% from 4). (7) NMR ($CDCl_3$) 7.99 (s, 0.5 H), 7.96 (s, 0.5 H), 6.94 (t, J=1.4 Hz, 1 H), 6.40 (m, 1 H), 6.05 (t, J=1.6 Hz), 5.27 (brs, 2 H), 5.10 (s, 1 H, 4' H), 3.82 (m, 1 H, 5'a), 3.67 (m, 1 H, 5'b), 1.71 (s, 3 H), 1.50 (s, 6 H).

Compound 7 (0.65 g, 1.64 mmol) was dissolved in methanol (2.0 ml), and saturated $K_2CO_3/H_2O$ was added at 0°. The suspension was stirred at room temperature for 2 h and extracted (EtOAc, 6×20 ml). The combined organic phase was washed (brine), dried ($Na_2SO_4$) and evaporated. White solid foam of 8 (450 mg, 97.8%). Total yield of 8 from 4 is 51.4% UVmax (MeOH): 220.5 nm, 247.0 nm, 309.0 nm. MS (FAB): Calc. for $C_{10}H_{11}Cl_1N_5O_2$ 268.0601; Found: 268.0678 (molecular ion peak for 6-bromopurine analogue was not found). NMR (DMSO-d6): 8.12 (s, 1H), 6.95 (br s, 2 H, $NH_2$), 6.80(s, 1 H), 6.40 (d, J=5.9 Hz, 1 H), 6.15 (d, J=5.9 Hz), 4.90 (t, 1 H, OH), 4.80 (s, 1 H, 4' H), 3.50 (br s, 2 H, 5' H).

2-Amino-6-cyclopropylamino-9-(2,3-dideoxy-β-D-glyceropent-2-enofuranosyl)purine (9) by the method of Crimmins, M. T. and King, B. W. *J. Org. Chem.* 1996, 61, 4192.

Compound 8 (0.32 g, 1.20 mmole) was dissolved in anhydrous ethanol (60 ml). Cyclopropylamine (5.5 ml, 80.0 mmole) was added. Stirring was continued at room temperature for 24 h. The solution was evaporated to dryness which was purified by silic gel chromatography eluting with $CHCl_3$/MeOH to give 9 (solid foam, 285 mg, 82.7%). UV (MeOH): 284.0 nm, 258.5 nm, 223.0 nm. NMR ($CDCl_3$): 0.61 (qd, 2 H), 0.82 (dd, 2 H), 2.95 (br. S, 1 H), 3.84 (dd, J=2.8, 12.8 Hz, 1 H), 4.04 (d, J=12.8 Hz, 1 H), 4.86 (brs, 2 H, $NH_2$), 5.06 (d, J=1.6 Hz, 1 H), 5.93 (d, J=6.0 Hz, 2 H, H-1' and H-$N_6$), 6.39 (dd, J=1.4, 6.0 Hz, 1 H, H-2'), 6.70 (dd, J=1.6, 3.7 Hz, H-3'), 7.49 (s, 1 H, H-8). MS: Calcd. for $C_{13}H_{16}N_6O_2$ 288.1361, Found: 289.1422 $(M+1)^+$ Elemental analysis, Calcd. C, 54.16; H, 5.59; N, 29.15; Found: C, 53.95; H, 5.43; N, 28.93.

Biological Experiments
Anti-HIV Activity

To assess the ability of the compounds according to the present invention to inhibit viral infection relative to other compounds experiments were performed in the MT-2 cell line, as previously described by Larder, et al., *Antimicrobial Agents & Chemotherapy*, vol. 34, 436 (1990). This T cell line is productively infected with Human T Cell Leukemia Virus (HTLV) and shows morphological and cytotoxic effects upon infection with HIV IIIB. Cells were infected at an initial multiplicity of infection (MOI) of 0.1 and grown for 5 days. Cell viability was assessed by the use of dye metabolized by viable cells. By plotting viability versus the amount of compound the concentration necessary to save 50% of the cells is determined ($EC_{50}$).

To determine the toxicity of the compounds to various cell lines (Table 1, below), a similar dye based assay is performed in the absence of HIV. The toxicity of the compounds alone therefore was determined. Various cell lines were grown in the presence of drug for 5 days at varying concentrations to see at what concentration the drug inhibited 50% of the cell growth ($IC_{50}$).

The results of these experiments are presented in Table I, below. Cd4G (compound 9, the prodrug of d4G, as prepared above) evidenced strong anti-HIV activity and reduced toxicity (in most cases, substantially and/or relatively non-toxic) to normal cells, an unexpected result given the complete inactivity of d4G to HIV and the level of toxicity displayed.

TABLE 1

AntiHIV activity* and toxicity[+] in MT-2 and various cell lines using MTT dye to determine cell viability.

| Nucleoside | MT-2[a] $EC_{50}$ (μM) | MT-2[a] $IC_{50}$ (μM) | CEM[b] $IC_{50}$ (μM) | HEP-G2[c] $IC_{50}$ (μM) | KB[d] $IC_{50}$ (μM) | HeLa[e] $IC_{50}$ (μM) |
|---|---|---|---|---|---|---|
| DdC | 0.3 ± 0.05 | 2 ± 0.3 | 3 ± 1 | 25 ± 2 | 100 ± 11 | >100 |
| DdI | 20 ± 6 | >>100 | >500 | >500 | >500 | 500 ± 33 |
| d4T | 3 ± 0.7 | >100 | 190 ± 30 | 390 ± 26 | 450 ± 47 | 480 ± 31 |
| d4G | NA | 40 ± 9 | 70 ± 11 | 280 ± 19 | >500 | 200 ± 13 |
| DAPD | 15 ± 4 | >>100 | >500 | 500 ± 33 | >500 | 500 ± 33 |
| Abacavir | 2 ± 0.4 | 60 ± 13 | 200 ± 50 | 180 ± 12 | 200 ± 21 | 500 ± 33 |
| Cd4G | 8 ± 2 | 100 ± 22 | 200 ± 31 | >500 | >500 | 500 ± 33 |

*NA = No Activity at concentrations up to 100 uM. $EC_{50}$ not achievable due to toxicity.
[a]HTLV infected T cell line
[b]T cell line
[c]Hepatoma cell line
[d]Oral Carcinoma
[e]Cervical Cancer Cell Line Mitochondrial Toxicity To address whether the compounds of the present invention exhibit mitochondrial toxicity and if so, to what extent, CEM cells were grown and passaged in the presence of different concentrations of drug. After 8 days of growth the cells were lysed and probed for the amount of mitochondrial DNA and normalized for differences in the amount of total DNA by probing for the Alu repeat. By comparing the amount of mitochondrial DNA to the amount of Alu repeat the % decrease in mitochondrial DNA in the presence of various concentrations of drug can be obtained. All experiments were done in triplicate. Techniques which are presented here have been previously described in Chen and Cheng, *J. Biol. Chem.*, vol. 264, 11934–7 (1989). The results, presented in Table 2, evidence that the d4G prodrug inhibited mitochrondrial DNA synthesis only at very high concentrations.

The results of the biological testing evidence that the compounds of the present invention exhibit marked anti-HIV activity and reduced toxicity at effective concentrations of the agents. Thus, compounds according to the present invention are potent and selective inhibitors of HIV and exhibit little, if any, relevant physiological toxicity. In fact, the activity exhibited by the cyclopropylamine prodrug (8 μM) is well within a range (between 0.3 and 20 μM) of preclinical and preclinical and FDA approved anti-HIV agents (Table 1). It was also found that the compound did not exhibit physiologically relevant toxicity in a wide variety of cells where the clinical concentration exceeded 40 μM (Table 1). This is an unexpected result, especially given the absence of activity and somewhat higher toxicity which is exhibited by d4G.

TABLE 2

Mitochondrial toxicity**. Ratio of mitochondrial DNA to Alu repeat[a] in the presence of various concentrations of compounds.

| Compound [μM] | Ration of mtDNA/Alu | % Control |
|---|---|---|
| Control | 1.07 ± 0.12 | — |
| DdC (0.01) | 0.93 ± 0.06 | 87 |
| DdC (0.1) | 0.70 ± 0.04 | 65 |
| DdC (1) | 0.03 ± 0.01 | 3 |
| D4T (1) | 1.18 ± 0.03 | 110 |
| d4T (10) | 1.00 ± 0.02 | 94 |
| d4T (200) | 0.22 ± 0.03 | 21 |
| Cd4G (1) | 1.06 ± 0.11 | 99 |
| Cd4G (10) | 0.90 ± 0.06 | 84 |
| Cd4G (200) | 0.46 ± 0.06 | 43 |
| d4G (1) | 1.12 ± 0.17 | 105 |
| d4G (10) | 1.14 ± 0.07 | 106 |
| Abacavir (1) | 1.18 ± 0.03 | 110 |
| Abacavir (10) | 1.27 ± 0.06 | 119 |
| Abacavir (200) | 1.36 ± 0.06 | 127 |

[a]An approximately 300 base pair transposable element containing a repeated sequence constituting about 5% of the human genome. Its abundance should not be affected by the presence of these nucleoside analogs.

Enzyme Kinetics

Continued research on the guanosine prodrug approach for making D4G a viable anti-HIV agent has yielded a number of new findings. In the present example, enzyme kinetics for the incorporation of the active metabolites of guanosine prodrugs with wild type HIV-1 reverse transcriptase was determined. In this experiment, a mixture of 100 nM HIV-1 reverse transcriptase and 300 nM primer/template in which the correct base incorporation is a guanine nucleotide was rapidly mixed with nucleotide in the presence of 50 mM Tris, 50 mM NaCl and 10 mM $MgCl_2$ for a set amount of time and then the reaction was stopped by the addition 300 mM of EDTA. The results of the experiment are set forth in Table 3, below.

TABLE 3

Kinetic constants for the incorporation of the active metabolites of guanosine prodrugs with wild type HIV-1 reverse transcriptase*.

| Substrate | dNTP | $k_{pol}$ (s$^{-1}$) | $K_d$ (μM) | $k_{pol}/K_d$ (s$^{-1}$μM) | Selectivity[a] |
|---|---|---|---|---|---|
| DNA/DNA | DGTP[b] | 24 ± 1 | 14 ± 2 | 1.7 ± 0.3 | 1 |
| | CBVTP[b] | 1.0 ± 0.06 | 21 ± 3 | 0.05 ± 0.01 | 30 |
| | DXGTP[c] | 1.46 ± 0.03 | 2.5 ± 0.2 | 0.58 ± 0.05 | 3 |
| | D4GTP | 11 ± 1 | 11 ± 2 | 1.1 ± 0.26 | 1.5 |
| DNA/RNA | DGTP[b] | 35 ± 2 | 11 ± 2 | 3.1 ± 0.6 | 1 |
| | CBVTP[b] | 1.5 ± 0.05 | 3.7 ± 0.5 | 0.42 ± 0.06 | 10 |
| | DXGTP[c] | 1.5 ± 0.1 | 8.8 ± 1.1 | 0.17 ± 0.02 | 20 |
| | D4GTP | 13 ± 0.5 | 9.5 ± 1.1 | 1.4 ± 0.2 | 2 |

[a]Selectivity = $(k_{pol}/K_d)^{dGTP}/(k_{pol}/K_d)^{analog}$.
[b]Ray and Anderson, "Mechanistic Studies to Understand the Inhibition of Wild Type and Mutant HIV-1 Reverse Transcriptase by Carbovir-Triphosphate,", Nucleosides, Nucleotides & Nucleic Acids, 20, (4–7) 1247–1250.
[c]Furman et al., Antimicrob. Agents Chemother., 45, 158–165, 2001.

Enzyme kinetics have shown that the probable active metabolite of the D4G prodrug of the present invention (D4GTP), is a better substrate for HIV-1 reverse transcriptase than are the active metabolites of DAPD (dXGTP) or Abacavir (CBVTP, table 3, above). Its high efficiency illustrates that it is better at mimicking dGTP in the active site and may indicate that it will be harder for drug resistant mutants to differentiate between it and the nature substrate. See, Vaccaro, et al., *Antimicrob. Agents Chemother.*, 44, 217-221, 1999. Evidence for this has been gleaned from an experiment performed with the commonly observed methionine 184 to valine mutation of reverse transcriptase, where it was found that there was no resistance conferred to D4GTP (see table 4, below). In contrast, experiments with CBVTP showed resistance.

Cell culture results have shown that cyclo-D4G of the present invention has lower mitochondrial toxicity than D4T. Kinetic experiments with purified mitochondrial polymerase support this observation as they evidence that D4GTP is a poorer substrate for incorporation by mitochondrial polymerase than is D4TTP and a better substrate for the exonuclease which could serve to unblock chain terminated mitochondrial transcripts and reverse toxic effects (table 5, below).

TABLE 4

Kinetic and equilibrium constants for binding and incorporation of dGTP, D4GTP and CBVTP by wild type and M184V HIV-1 RT*.

| Primer/template | RT | Nucleotide | $K_{pol}$ (s$^{-1}$) | $K_d$ (μM) | Efficiency (s$^{-1}$μM$^{-1}$) | Selectivity[a] |
|---|---|---|---|---|---|---|
| DNA/DNA | RT$^{WT}$ | DGTP | 24 ± 1 | 14 ± 2 | 1.7 ± 0.3 | — |
| | | D4GTP | 11 ± 1 | 11 ± 2 | 1.1 ± 0.3 | 2 |
| | | CBVTP | 1.0 ± 0.06 | 21 ± 3 | 0.05 ± 0.01 | 30 |
| | RT$^{M184V}$ | dGTP | 35 ± 1 | 16 ± 2 | 2.2 ± 0.3 | — |
| | | D4GTP | 8.6 ± 0.4 | 9.3 ± 1.2 | 0.93 ± 0.13 | 2 |
| | | CBVTP | 0.45 ± 0.02 | 51 ± 5 | 0.009 ± 0.001 | 200 |
| DNA/RNA | RT$^{WT}$ | dGTP | 35 ± 2 | 11 ± 2 | 3.1 ± 0.6 | — |
| | | D4GTP | 13 ± 0.5 | 9.5 ± 1.1 | 1.4 ± 0.2 | 2 |
| | | CBVTP | 1.5 ± 0.05 | 3.7 ± 0.5 | 0.42 ± 0.06 | 10 |
| | RT$^{M184V}$ | dGTP | 120 ± 13 | 42 ± 10 | 2.9 ± 0.8 | — |
| | | D4GTP | 17 ± 0.8 | 13 ± 2 | 1.7 ± 0.27 | 2 |
| | | CBVTP | 0.65 ± 0.06 | 38 ± 7 | 0.017 ± 0.004 | 200 |

[a]Selectivity = efficiency$_{dGTP}$/efficiency$_{analog}$
Enzymatic assays done similar to those of Table 3.

TABLE 5

Kinetic constants for the incorporation of the natural nucleotide and their 2',3' dideoxy-2',3'-didehydro analogs by mitochondrial polymerase gamma into an elongating DNA strand*.

| Nucleotide | $k_{pol}$ ($s^{-1}$) | $K_d$ ($\mu M$) | $K_{pol}/K_d$ ($\mu M^{-1}s^{-1}$) | Discrimination[a] | $k_{exo}$ ($s^{-1}$) | Toxicity Index[c] |
|---|---|---|---|---|---|---|
| dTTP | 25 ± 2 | 0.60 ± 0.16 | 39 ± 13 | — | ND | — |
| D4TTP[b] | 0.24 ± 0.01 | 0.045 ± 0.0075 | 5.4 ± 0.93 | 7.4 | 0.0004 | 3,120 |
| dGTP | 175 ± 10 | 1.4 ± 0.3 | 130 ± 30 | — | 0.019 ± 0.0019 | — |
| D4GTP | 0.27 ± 0.02 | 0.61 ± 0.13 | 0.45 ± 0.099 | 300 | 0.00046 ± 0.000021 | 320 |

[a]Discrimination = $(k_{pol}/K_d)^{dGTP}/(k_{pol}/K_d)^{analog}$
[b]Johnson et al. In press, Journal of Biological Chemistry.
[c]Toxicity Index = $1 + [(k_{cal}/k_{exo}) \times ([AnaTP]/[dNTP])/4*D]$. Equation reflects the fold increase in time that it would take for mitochondrial replication. A value of 1 would indicate no toxicity.
*Incorporation experiments were done similar to those with HIV-1 reverse transcriptase. Large (catalytic) and small mitochondrial polymerase gamma subunits were mixed with a 5-fold excess of the small subunit. This mixture (50 nM Large Subunit) was then preincubated with 250 nM primer template and mixed with 5 mM $MgCl_2$ and nucleotide with 50 mM Tris and 100 mM NaCl. After a set incubation period the reaction was stopped by the addition of 0.3 M EDTA. For exonuclease studies, 75 nM chain terminated primer template was mixed with 100 nM Large and 400 nM small mitochondrial polymerase gamma subunits in the presence of 2.5 mM $MgCl_2$, 50 mM Tris and 100 mM NaCl. Reactions were stopped by the addition of 0.3 M EDTA.

Cell Culture

Figure 2:
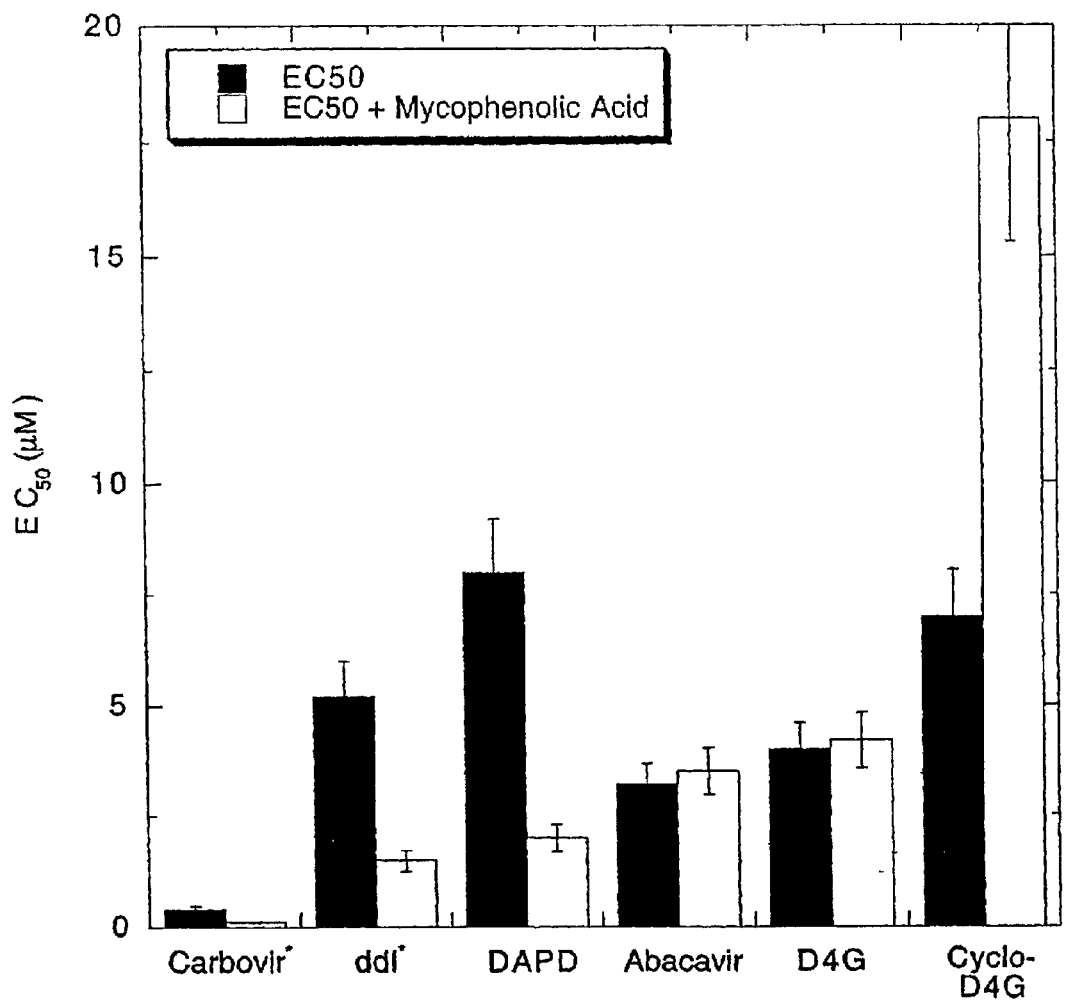
FIG. 2 presents table 6 and indicates the effect that mycophenolic acid has on the anti-HIV activity of the indicated nucleoside analogs. In the experiment depicted in this Figure, $1 \times 10^5$ cells/ml were incubated with or without 200 nM mycophenolic acid for 30 minutes and then added to wells containing nucleoside analogs to test for toxicity and anti-HIV activity. The date presented is representative of at least two independent trials.

In cell culture, the mechanism of activation for D4G prodrugs has been investigated with the initial model compound cyclo D4G. It has been found that this compound is activated by a deaminase dependent pathway similar to other guanosine prodrugs (DAPD and Abacavir). However, unlike Abacavir and DAPD, it has been found that this compound's anti-HIV activity is dependent on the presence of a guanine-containing agent. Experiments with mycophenolic acid, an inhibitor of inosine monophosphate (IMP) dehydrogenase have been used to study the guanine dependence of activation for cyclo D4G. The addition of mycophenolic acid results in an increase in cellular IMP and a decrease in GMP and all other guanine containing nucleosides and nucleotides. Unlike a panel of compounds that showed no effect or an increase in activity, cyclo D4G was found to be 3-fold less active in the presence of mycophenolic acid (see Table 6, in attached FIG. 2) in an experiment in which $1\times10^5$ cells/ml were incubated with or without 200 nM mycophenolic acid for 30 minutes and then added to wells containing nucleoside analogs to test for toxicity and anti-HIV activity. The data which is presented is representative of at least two independent trials. Furthermore, cyclo D4G's activity could be rescued by the addition of guanine to the media (data not shown).

Combination Therapy

Figure 3:
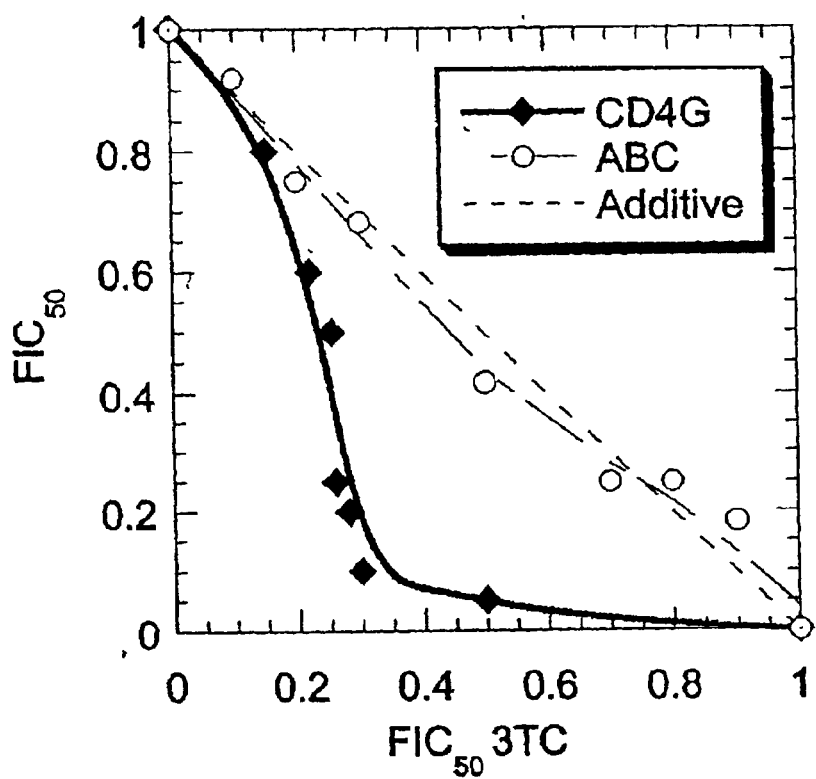
FIG. 3 presents a comparison of the anti-HIV synergy which is produced when 3TC is used in combination with abacavir or cyclo D4G of the present invention. The date presented results from two independent trials performed in triplicate.
Figure 4:
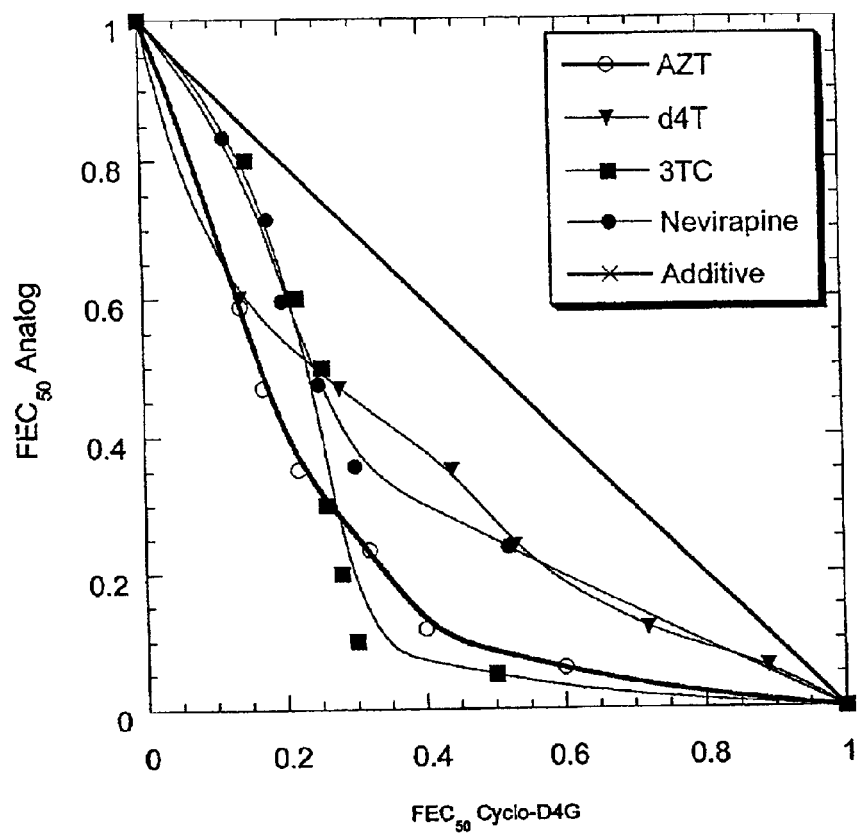
FIG. 4 presents a comparison of the anti-HIV synergy which is produced when several FDA approved anti-HIV nucleoside analogs are combined with cyclo D4G of the present invention. In this experiment, AZT, d4T, 3TC and Nevirapine were tested for their anti-HIV activity in combination with cyclo D4G. The fraction of the effective concentration capable of rescuing 50% of the cells from infection ($FEC_{50}$) was then plotted for each nucleoside versus the $FEC_{50}$ of cyclo d4G. Synergy is defined by points that lie significantly below a line connecting the points which correspond to the activity of each compound on its own. Points on this line represent the compounds working independently.

Combination therapy has proven to be the most effective method to fight HIV infection. In an attempt to understand how D4G prodrugs of the present invention would interact with other clinically approved compounds, experiments were performed with drug combinations. It was found in cell culture that a combination of cyclo D4G and 3TC was synergistic in inhibiting HIV, whereas a combination of abacavir and 3TC was merely additive. See FIG. 3. Further testing evidenced that cyclo D4G is synergistic with 3TC, AZT and somewhat synergistic with D4T (FIG. 4). In the experiment presented in FIG. 4, 3TC, D4T and AZT were tested for their anti-HIV activity in combination with cyclo D4G. The fraction of the effective concentration capable of rescuing 50% of the cells from infection ($FEC_{50}$) was then plotted for each nucleoside versus the FEC50 of cyclo D4G. Synergy is defined by points that lie significantly below a line connecting the points which correspond to the activity of each compound on its own. Points on the line represent two compounds working independently. The results evidence that all of these drugs could be given as effective combination treatments for HIV. The cyclo D4G, AZT combination is particularly interesting in that it presents the opportunity to combine a 2',3' dideoxy 2',3' didehydro ribose modified nucleoside analog with AZT. Note, in contrast, that D4T and AZT combination therapy has proven ineffective and in cell culture it was found that D4T and AZT are only additive (data not shown). Current research also shows that two analogs of the same base (i.e., D4T and AZT, 3TC and ddC, FD4C and 3TC, abacavir and cyclo D4G) are not synergistic. See, Bridges, et al., *Biochem. Pharmacol.*, 51, 731 (1996) and Dutschman, et al., *Antimicro. Agents Chemother.* 42, 1799 (1998). When compared with isobolograms generated with abacavir, it appears that cyclo D4G is substantially more effective in combination with 3TC and D4T. These results evidence that cyclo D4G has characteristics which could be advantageous in combination therapy and in some cases is superior to FDA approved drugs.

It is to be understood by those skilled in the art that the foregoing description and examples are illustrative of practicing the present invention, but are in no way limiting. Variations of the detail presented herein may be made without departing from the spirit and scope of the present invention as defined by the following claims.

References

1. De Clercq, E. (1995) *J. Med. Chem.* 38, 2491–2517.
2. De Clercq, E. (1997) *Clin. Microbiol. Rev.* 10, 674–693.
3. Mitsuya, H., Yarchoan, R., Kageyama, S., and Broder, S. (1991) *FASEB J.* 5, 2369–2381.
4. Parker, W. B., and Cheng, Y. C. (1994) *J. of NIH Research* 6, 57–61.
5. Martin, J. L., Brown, C. E., Matthews-Davis, N., and Reardon, J. E. (1994) *Antimicrob. Agents &.Chemother.* 38, 2743–2749.
6. Larder, B. A. (1994) *J. Gen. Virol.* 75, 951–957.
7. Daluge, S. M., Good, S. S., Faletto, M. B., Miller, W. H., St. Clair, M. H., Boone, L. R., Tisdale, M., Parry, N. R., Reardon, J. E., Dornsife, R. E., Averett, D. R., and Krenitsky, T. A. (1997) *Antimicrob. Agents Chemother.* 41, 1082–1093.
8. Faletto, M. B., Miller, W. H., Garvey, E. P., St. Clair, M. H., Daluge, S. M., and Good, S. S. (1997) *Antimicrob. Agents Chemother.* 41, 1099–1107.
9. Parker, W. B., Shaddix, S. C., Bowdon, B. J., Rose, L. M., Vince, R., Shannon, W. M., and Bennett, L. L., Jr. (1993) *Antimicrob. Agents Chemother.* 37, 1004–9.

10. Vince, R., Hua, M., Brownell, J., Daluge, S. M., Lee, F. C., Shannon, W. M., Lavelle, G. C., Qualls, J., Weislow, O. S., Kiser, R., Canonico, P. G., Schultz, R. H., Narayanan, V. L., Mayo, J. G., Shoemaker, R. H., and Boyd, M. R. (1988) *Biochem. Biophys. Res. Commun.* 156, 1046–1053.

11. Vince, R., and Hua, M. (1990) *J. Med. Chem.* 1, 17–21.

12. Wolbach, J., and Capoccia, K. (1999) *Nurse Pract.* 24, 81–2, 87–90, 92.

13. Foster, R. H., and Faulds, D. (1998) *Drugs* 55, 729–36; discussion 737–8.

14. Tisdale, M., Alnadaf, T., and Cousens, D. (1997) *Antimicrob. Agents Chemother.* 41, 1094–8.

15. Mellors, J. W., Hertogs, K., Peeters, F., and al, e. (1998) in *Fifth Conference on Retroviruses and Opportunistic infections*, Chicago, IL.

16. White, E. L., Parker, W. B., Macy, L. J., Shaddix, S. C., McCaleb, G., Secrist III, J. A., Vince, R., and Shannon, W. M. (1989) *Biochem. Biophys. Res. Commun.* 161, 393–398.

17. Parker, W. B., White, E. L., Shaddix, S. C., Ross, L. J., Buckheit, R. W., Germany, J. M., Secrist, J. A., Vince, R., and Shannon, W. M. (1991) *J. Biol. Chem.* 266, 1754–1762.

18. Harrigan, P. R., Stone, C., Griffin, P., Najera, I., Bloor, S., Kemp, S., Tisdale, M., and Larder, B. (2000) *J. Infect. Dis.* 181, 912–920.

19. Miller, V., Ait-Khaled, M., Stone, C., Griffin, P., Mesogiti, D., Cutrell, A., Harrigan, R., Staszewski, S., Katlama, C., Pearce, G., and Tisdale, M. (2000) *Aids* 14, 163–71.

20. Schinazi, R. F., Lloyd, R. M., Jr., Nguyen, M. H., Cannon, D. L., McMillan, A., Ilksoy, N., Chu, C. K., Liotta, D. C., Bazmi, H. Z., and Mellors, J. W. (1993) *Antimicrob. Agents &.Chemother.* 37, 875–881.

21. Schuurman, R., Nijhuis, M., van Leeuwen, R., Schipper, P., Collis, P., Danner, S. A., Mulder, J., Loveday, C., Christopherson, C., Kwok, S., Sninsky, J., and Boucher, C. A. B. (1995) *J. Infect. Dis.* 171, 1411–1419.

22. Feng, J. Y., and Anderson, K. S. (1999) *Biochemistry* 38, 9440–8.

23. Orr, D. C., Figueiredo, H. T., Mo, C. L., Penn, C. R., and Cameron, J. M. (1992) *J. Biol. Chem.* 267, 4177–82.

24. Kati, W. M., Johnson, K. A., Jerva, L. F., and Anderson, K. S. (1992) *J. Biol. Chem.* 267, 25988–25997.

25. Chu, et al., *Biochem. Pharm.* (1988) 37, 3543–3548.

26. Perelson, et al., *Science*, (1996) 271, 1582–1586.

27. Gao, et al., *J. Bio. Chem.* (1994), 269,12633–12638.

28. Harrigan, et al., *J. Infect. Dis.*, (2000) 181, 912–920.

29. Miller, et al., *Aids*, (2000) 14, 163–171.

30. Schinazi, et al., *Antimicrob. Agents Chemother.*, (1993) 37, 875–881.

31. Tisdale, et al., *Antimicrob. Agents Chemother.*, (1997) 41, 1094–1098.

32. Tisdale, et al., *PNAS*, 90, 5653–5656.

33. Ray, et al., *Antimicrob. Agents Chemother.*, 46, (3) in press.

What is claimed is:

1. A compound according to the structure:

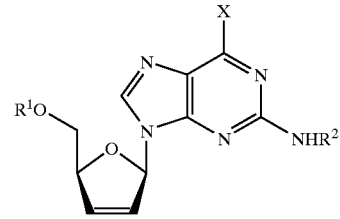

where X is $N_3$, $NHCH_3$, $N(CH_3)_2$ or an aminocyclopropyl group;

$R^1$ is H or a $C_1$ to $C_{20}$ acyl or alkyl group, a phosphate, diphosphate, triphosphate or phosphodiester group; and $R^2$ is H or $C_1$ to $C_{20}$ acyl or alkyl group or a pharmaceutically acceptable salt thereof.

2. The compound according to claim 1 wherein X is an aminocyclopropyl group.

3. A pharmaceutical composition comprising an anti-HIV effective compound according to the structure:

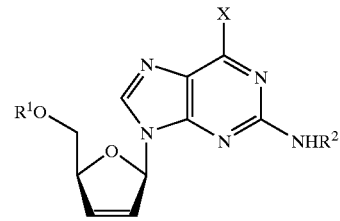

where X is $OCH_3$, $N_3$, $NHCH_3$, $N(CH_3)_2$ or an aminocyclopropyl group;

$R^1$ is H or a $C_1$ to $C_{20}$ acyl or alkyl group, a phosphate, diphosphate, triphosphate or phosphodiester group; and $R^2$ is H or a $C_1$ (acetyl) to $C_{20}$ acyl or alkyl group or a pharmaceutically acceptable salt thereof, optionally in combination with a pharmaceuticaily acceptable carrier, additive or excipient.

4. The composition according to claim 3 wherein X is an aminocyclopropyl group and $R^1$ and $R^2$ are H.

5. A pharmaceutical composition comprising a combination of an effective amount of a compound according to the structure:

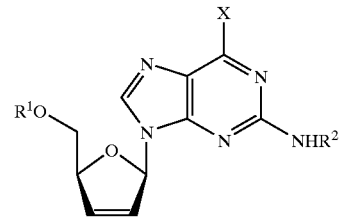

where X is $OCH_3$, $N_3$, $NHCH_3$, $N(CH_3)_2$ or an aminocyclopropyl group;

$R^1$ is H or a $C_1$ to $C_{20}$ acyl or alkyl group, a phosphate, diphosphate, triphosphate or phosphodiester group; and $R^2$ is H or a $C_1$ to $C_{20}$ acyl or alkyl group or a pharmaceutically acceptable salt thereof; and at least one additional agent selected from the group consisting of a nucleoside reverse transcriptase inhibitor, a non-nucleoside reverse transcriptase inhibitor, a protease inhibitor, a HIV zinc finger inhibitor, a cell cycle inhibitor, a cytotoxic agent, an HIV integrase inhibitor, a nucleocapsid inhibitor, and a viral entry inhibitor, optionally in combination with a pharmaceutically acceptable carrier, additive or excipient.

6. The composition according to claim 5 wherein X is an aminocyclopropyl group and $R^1$ and $R^2$ are H.

7. The composition of claim 5 wherein said additional agent is a nucleoside reverse transcriptase inhibitor selected from the group consisting of AZT, 3TC, ddC, FTC, D4FC, D4T, ddI, PMPA, Bis(POC)PMPA and mixtures thereof.

8. The composition of claim 5 wherein said additional agent is a non-nucleoside reverse transcriptase inhibitor selected from the group consisting of Nevirapine, Delavirdine, Efavirenz, Emivirine, TIBO, GW420867X, UC 781 and mixtures thereof.

9. The composition of claim 5 wherein said additional agent is a protease inhibitor selected from the group consisting of Saquinavir, Amprenavir, Indinavir, Nelfinavir, Ritonavir, Tipranavir, Lopinavir, GW433 908, Lasinavir and mixtures thereof.

10. The composition of claim 5 wherein said additional agent is selected from the group consisting of 1,1'-azobisformamide, hydroxyurea, LiGLA, and mixtures thereof.

11. A method for inhibiting the growth, elaboration and/or the replication of HIV in a patient comprising administering to said patient an anti-HIV effective amount of a compound according to the structure:

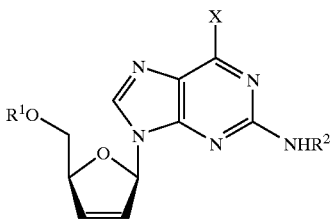

where X is $OCH_3$, $N_3$, $NHCH_3$, $N(CH_3)_2$ or an amniocyclopropyl group;

$R^1$ is H or a $C_1$ to $C_{20}$ acyl or alkyl group, a phosphate, diphosphate, triphosphate or phosphodiester group; and $R^2$ is H or a $C_1$ to $C_{20}$ or alkyl group or a pharmaceutically acceptable salt thereof, optionally in combination with a pharmaceutically acceptable carrier, additive or excipient.

12. The method according to claim 11 wherein X is an aminocyclopropyl group and $R^1$ and $R^2$ are H.

13. A method for inhibiting the growth, elaboration and/or the replication of HIV in a patient comprising administering to said patient a combination of an anti-HIV effective amount of a compound according to the structure:

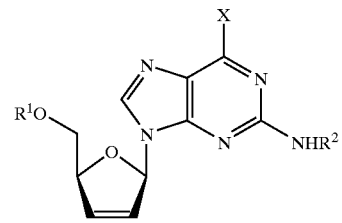

where X is $OCH_3$, $N_3$, $NHCH_3$, $N(CH_3)_2$ or an aminocyclopropyl group;

$R^1$ is H or a $C_1$ to $C_{20}$ acyl or alkyl group, a phosphate, diphosphate, triphosphate or phosphodiester group; and $R^2$ is H or a $C_1$ to $C_{20}$ acyl or alkyl group or a pharmaceutically acceptable salt thereof; and at least one additional agent selected from the group consisting of a nucleoside reverse transcriptase inhibitor, a non-nucleoside reverse transcriptase inhibitor, a proteaso inhibitor, a HIV zinc finger inhibitor, a cell cycle inhibitor, a cyotoxic agent, an HIV integrase inhibitor, a nucleocapsid inhibitor, and a viral entry inhibitor, optionally in combination with a pharmaceutically acceptable carrier, additive or excipient.

14. The method according to claim 13 wherein X is an aminocyclopropyl group and $R^1$ and $R^2$ are H.

15. The method of claim 13 wherein said additional agent is a nucleoside reverse transcriptase inhibitor selected from the group consisting of AZT, 3TC, ddC, FTC, D4FC, D4T, ddI, PMPA, Bis(POC)PMPA and mixtures thereof.

16. The method of claim 13 wherein said additional agent is a non-nucleoside reverse transcriptase inhibitor selected from the group consisting of Nevirapine, Delavirdine, Efavirenz, Emivirine, TIBO, GW420867X, UC 781 and mixtures thereof.

17. The method of claim 13 wherein said additional agent is a protease inhibitor selected from the group consisting of Saquinavir, Amprenavir, Indinavir, Nelfinavir, Ritonavir, Tipranavir, Lopinavir, GW433 908, Lasinavir and mixtures thereof.

18. The method of claim 13 wherein said additional agent is selected from the group consisting of 1,1'-azobisformamide, hydroxyunrea, LiGLA, and mixtures thereof.

19. The method of claim 14 wherein said additional agent is a nucleoside reverse transcriptase inhibitor selected from the group consisting of AZT, 3TC, ddC, FTC, D4FC, D4T, ddI, PMPA, Bis(POC)PMPA and mixtures thereof.

20. The method according to claim 14 wherein said additional agent is selected from the group consisting of AZT, 3TC and mixtures thereof.

\* \* \* \* \*

UNITED STATES PATENT AND TRADEMARK OFFICE
CERTIFICATE OF CORRECTION

PATENT NO. : 6,900,315 B2  
DATED : May 31, 2005  
INVENTOR(S) : Anderson et al.

Page 1 of 1

It is certified that error appears in the above-identified patent and that said Letters Patent is hereby corrected as shown below:

<u>Title page,</u>  
Item [73], Assignee, should read:  
-- Assignee: Yale Unviversity, New Haven, CT (US)  
          University of Georgia Research Foundation, Inc., Athens, GA (US) --.

Signed and Sealed this

Sixteenth Day of August, 2005

JON W. DUDAS  
*Director of the United States Patent and Trademark Office*